(12) United States Patent
Vetere et al.

(10) Patent No.: US 7,603,890 B2
(45) Date of Patent: Oct. 20, 2009

(54) METHOD OF INSPECTING A METAL ALLOY PART FOR INCIPIENT MELTING

(75) Inventors: Thomas A. Vetere, Bedford, TX (US); Stephen M. Kurpaska, Newington, CT (US); Edward R. Szela, West Springfield, MA (US); John M. Robertson, Lake Spivey, GA (US)

(73) Assignee: United Technologies Corporation, Hartford, CT (US)

( * ) Notice: Subject to any disclaimer, the term of this patent is extended or adjusted under 35 U.S.C. 154(b) by 0 days.

(21) Appl. No.: 12/072,189

(22) Filed: Feb. 25, 2008

(65) Prior Publication Data
US 2008/0308959 A1 Dec. 18, 2008

(51) Int. Cl.
*G01N 19/08* (2006.01)
(52) U.S. Cl. ..................................................... 73/104
(58) Field of Classification Search .................. 73/104, 73/5; 264/39, 40.1, 300; 252/408.1, 960; 356/237.2
See application file for complete search history.

(56) References Cited

U.S. PATENT DOCUMENTS

| | | | | |
|---|---|---|---|---|
| 2,601,703 A | * | 7/1952 | Sawyer | 264/40.1 |
| 2,984,101 A | * | 5/1961 | Minor et al. | 73/104 |
| 3,862,047 A | * | 1/1975 | Weltman et al. | 252/62.52 |
| 4,008,844 A | | 2/1977 | Duvall et al. | |
| 4,043,187 A | * | 8/1977 | Tomomatsu | 73/105 |
| 4,198,362 A | * | 4/1980 | Ticker et al. | 264/40.1 |
| 4,560,578 A | * | 12/1985 | Freeman | 427/504 |
| 5,610,326 A | * | 3/1997 | Leost | 73/105 |
| 5,806,751 A | | 9/1998 | Schaefer et al. | |
| 6,367,686 B1 | | 4/2002 | Abriles et al. | |
| 6,503,349 B2 | | 1/2003 | Pietruska et al. | |
| 6,508,000 B2 | | 1/2003 | Burke et al. | |
| 6,530,971 B1 | | 3/2003 | Cohen et al. | |
| 6,575,349 B2 | | 6/2003 | Van Esch | |
| 7,156,280 B1 | | 1/2007 | Jiang et al. | |
| 2003/0228418 A1 | * | 12/2003 | Hines et al. | 427/256 |

(Continued)

FOREIGN PATENT DOCUMENTS

JP           59079832 A    *    5/1984

(Continued)

OTHER PUBLICATIONS

Hoffman et al., "Use of Surface Replication, Extraction Replication, and Thin-Film Electron Microscopy in the Study of Dispersion-Strengthened Materials," Mar. 1968, NASA TN D-4461, pp. 1-27.*

(Continued)

*Primary Examiner*—John Fitzgerald
(74) *Attorney, Agent, or Firm*—Kinney & Lange, P.A.

(57) ABSTRACT

A method of inspecting a repaired metal alloy part to analyze a microstructure of the metal part includes placing a replicating material on a surface of the metal part to create an inverted replica of the microstructure. The replicating material is then removed from the surface. An image of the inverted replica on the replicating material is magnified in order to evaluate the microstructure for incipient melting and areas of boride concentration. This inspection method facilitates that evaluation without causing any destruction to the metal part.

26 Claims, 4 Drawing Sheets

U.S. PATENT DOCUMENTS

2006/0248718 A1 11/2006 Szela et al.
2008/0173078 A1* 7/2008 Christ et al. .................. 73/104

FOREIGN PATENT DOCUMENTS

| JP | 02170010 | A | * | 6/1990 |
| JP | 03221831 | A | * | 9/1991 |
| JP | 04012242 | A | * | 1/1992 |
| JP | 04249701 | A | * | 9/1992 |
| JP | 05045266 | A | * | 2/1993 |

OTHER PUBLICATIONS

Kalab, "Replication and scanning electron microscopy of metal surfaces used in food processing," Jan. 25, 2005, Web document, pp. 1-4.*

McGuigan, "Surface Replication of Power Plant Components," Dec. 1994, Life management of power plants, Conference Publication No. 401.*

Electron Microscopy Sciences—Technical Data Sheets: "Replicating Sheet—Cellulose Acetate Film", from http://www.emsdiasum.com/microscopy/technical/datasheet/50420.aspx, visited Jan. 18, 2007 (1 page).

Electron Microscopy Sciences: "Material Science and Metrology", from http://www.emsdiasum.com/microscopy/products/materials/replicating.aspx, visited May 30, 2007 (2 pages).

Ted Pella, Inc.: "Replication Materials", from http://www.tedpella.com/replicat_html/44840.htm, visited Feb. 28, 2007 (2 pages).

"Acetate Cellulose Replicating Film", PELCO® Technical Notes, Replicating Sheet—link from http://www.tedpella.com/replicat_html/44840.htm, visited Feb. 28, 2007 (2 pages).

SPI Supplies: "SPI Replicating Tapes and Sheets", from http://www.2spi.com/catalog/submat/cellulose-acetate-replicating-tape-sheets.shtml, visited Feb. 28, 2007 (3 pages).

Material Safety Data Sheet for Collodion, U.S.P., from http://jbaker.com/msds/englishhtml/c5060.htm, visited May 23, 2007 (9 pages).

* cited by examiner

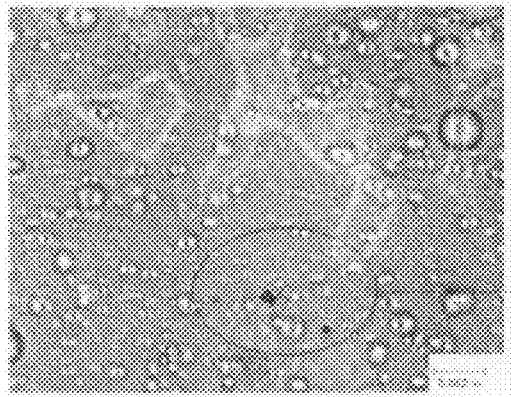
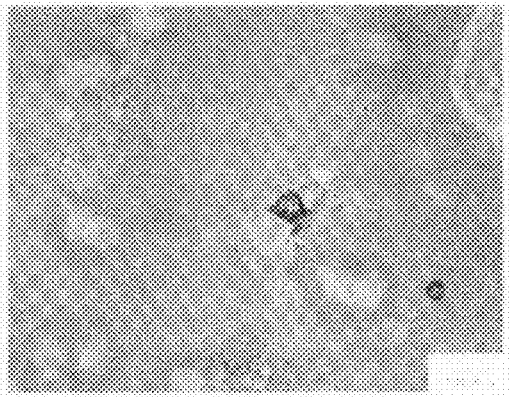
Fig. 3A    Fig. 3B
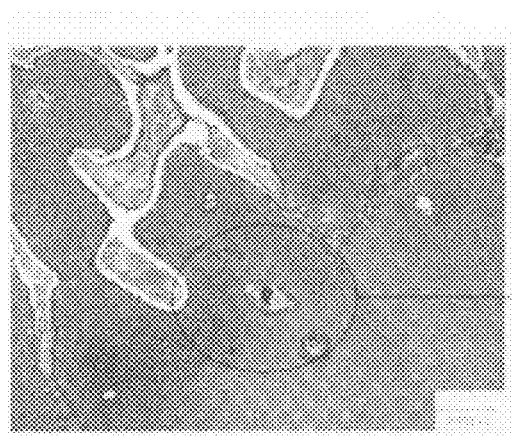
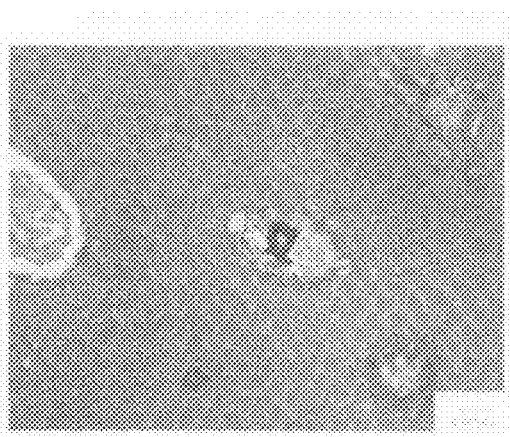
Fig. 4A    Fig. 4B

METHOD OF INSPECTING A METAL ALLOY PART FOR INCIPIENT MELTING

CROSS-REFERENCE TO RELATED APPLICATION(S)

Reference is made to the following pending application: U.S. patent application Ser. No. 11/820,162, entitled "A METHOD OF DETERMINING DEPTH OF INTRAGRANULAR ATTACK (IGA) FOR A METAL PART", and filed on Jun. 18, 2007.

BACKGROUND

The present invention relates to a method of replicating a microstructure of a metal alloy part. More particularly, the present invention relates to an inspection method for determining a presence of incipient melting in a metal alloy part, such as those used in an aircraft engine.

Metal parts may be prone to developing cracks, especially when exposed to extreme conditions. For example, a gas turbine engine operates at extreme temperatures and pressures. Many of the engine parts may be made of nickel-based alloys and other high temperature alloys that are able to withstand the high operating temperatures. Even when high temperature alloys are used, the engine parts (such as, for example, vanes) may crack. A repair process for a vane within an assembly includes filling the cracks with a metal alloy and then heat treating the vane assembly. This repair process, known as a braze alloy repair, commonly lowers an incipient melting temperature of the base metal alloy that forms the engine part. This is because the braze alloy material contains boron, which acts as a melting point suppressant, so the braze material melts at a lower temperature and is able to fill the cracks in the base metal alloy. As a result of a diffusion of boron into the base metal alloy, incipient melting of the base metal alloy may occur during the repair process. After a melted area of the metal alloy then cools and re-solidifies, voids or pores form in a microstructure of the metal alloy, which compromises the integrity of the metal alloy part.

In some cases, once a part has undergone one braze repair and returned to service, the part may not be repaired again once it is removed from service a second time. This is due, in part, to the risk that incipient melting may have occurred during the first crack repair. The part is thus deemed non-repairable, and in some cases, may be scrapped after it is removed from operation. In other cases, the part may be permitted to undergo a second, or even a third, braze repair. However, the part must first undergo expensive and lengthy testing, which includes an evaluation to determine if incipient melting has occurred, in which case the part likely should not undergo an additional repair.

There is a need for an improved method of inspecting metal alloy parts for incipient melting to easily and economically determine if a part is in a condition to undergo a braze repair and be returned to service.

SUMMARY

The present invention relates to a non-destructive method of inspecting a repaired metal alloy part to analyze a microstructure of the part. In some embodiments, the repaired metal part is a component of a gas turbine engine, such as a vane assembly. The engine parts may undergo a crack repair process that introduces boron into the base metal alloy. Diffusion of boron into the base metal alloy may lower an incipient melting point of the metal alloy, and incipient melting of the metal alloy may occur. Once the melted portion of the metal alloy cools and re-solidifies, voids or pores form in the microstructure of the metal, which may have a negative impact on integrity of the metal alloy. Before the repair process may be performed, the microstructure of the metal alloy is evaluated. In other known methods, it may have been necessary to sacrifice or compromise a part in order to complete this evaluation.

The non-destructive method here includes placing a replicating material on a surface of the metal part to create an inverted replica of a microstructure of the surface. The replicating material is then removed from the surface. In an exemplary embodiment, the replicating material is a cellulose acetate film. An image of the inverted replica on the replicating material is magnified in order to evaluate the microstructure for incipient melting (i.e. voids in the metal alloy). The voids are visible as dark spots on the magnified image and commonly appear in proximity to boride-concentrated areas. The replicated image may be compared to a set of metal alloy samples that include samples that are in condition for repair and samples that are deemed non-repairable due to incipient melting. In some embodiments, any amount of incipient melting is unacceptable. In some cases, samples classified as being in condition for repair may include areas of boride concentration so long as voids are not present. Based on a comparison of the replicated image with the set of samples, a determination is made as to whether the metal part may be returned to service in a gas turbine engine after the crack repair process.

BRIEF DESCRIPTION OF THE DRAWINGS

FIGS. 3A and 3B are magnified photographs of a replicated image of a microstructure of a metal alloy part.

FIGS. 4A and 4B are magnified photographs of a micro or sample that was removed from a metal alloy part.

DETAILED DESCRIPTION

Figure 1A:
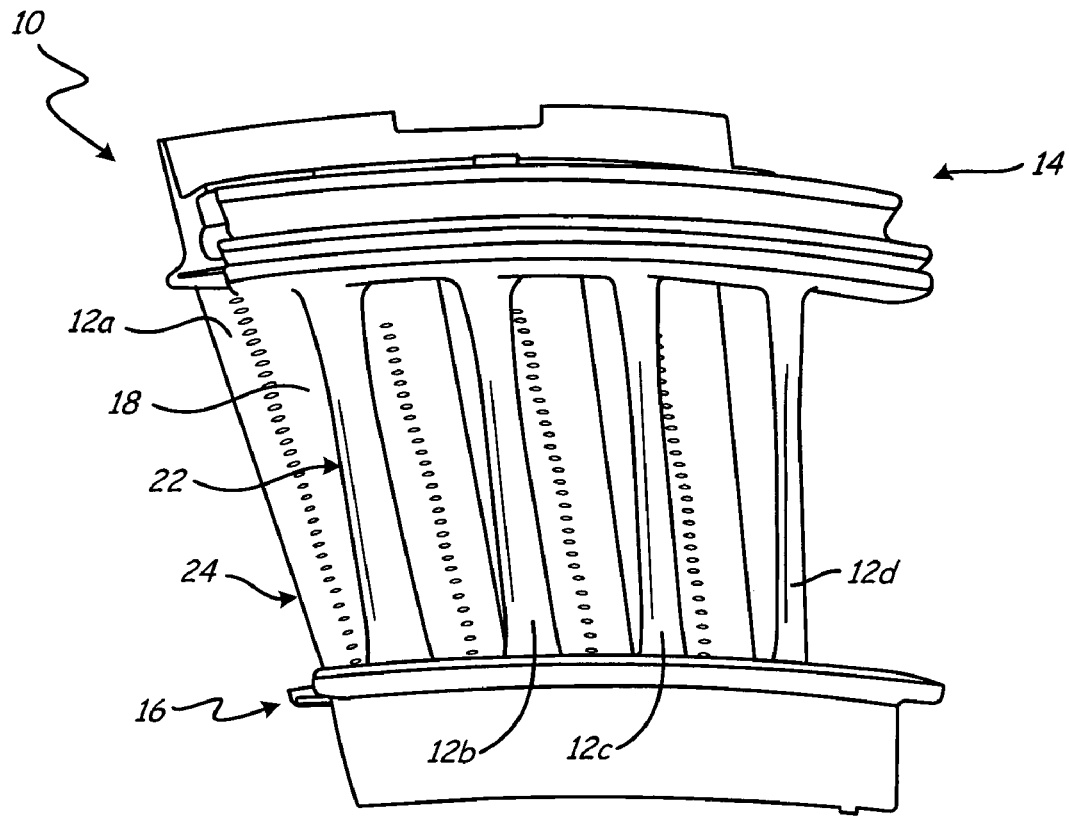
FIG. 1A is a perspective view of a vane assembly for use in a gas turbine engine.
Figure 1B:
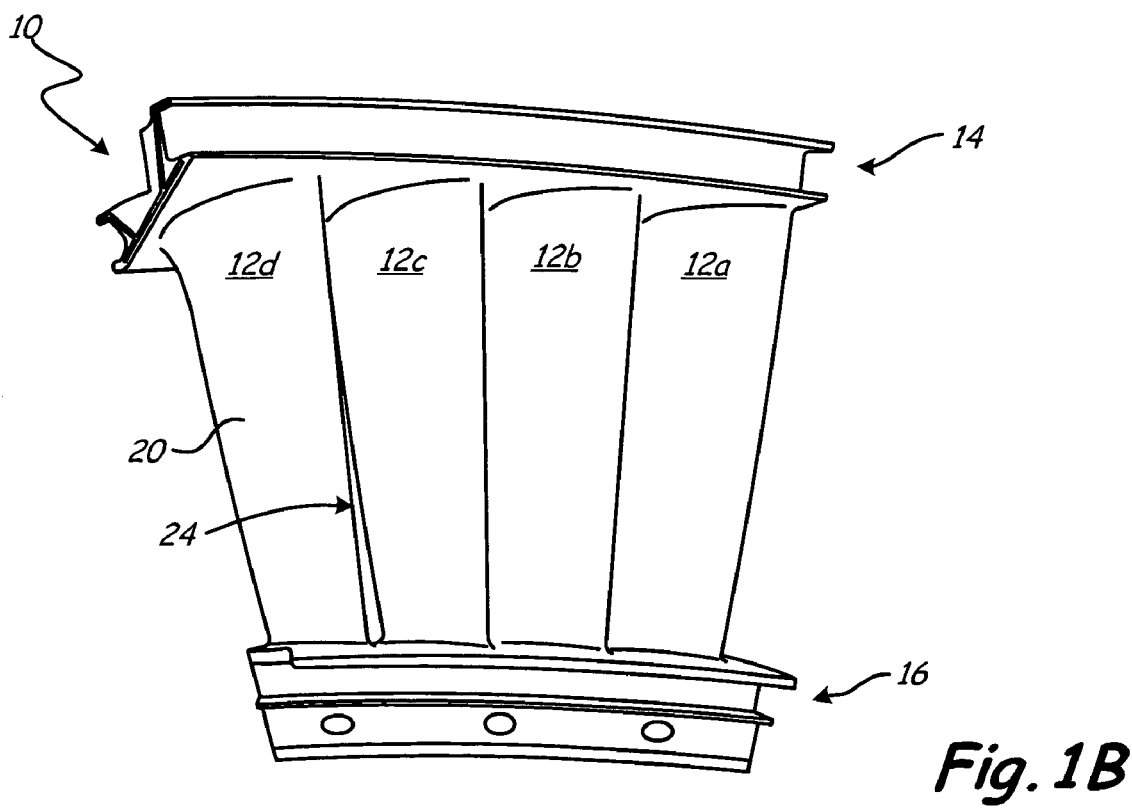
FIG. 1B is a perspective view of the vane assembly of FIG. 1A rotated approximately 180 degrees.

FIGS. 1A and 1B are perspective views of vane assembly 10, which may be part of a low pressure turbine or a high pressure turbine, both of a gas turbine engine. Vane assembly 10 may also be referred to as a nozzle segment, and may be formed by casting of a metal alloy, such as, for example, a nickel alloy. Vane assembly 10 includes vanes 12 (also known as airfoils), shroud 14 and platform 16. In the embodiment of FIGS. 1A and 1B, vane assembly 10 includes four vanes 12a, 12b, 12c and 12d. Each of vanes 12 includes pressure side 18, suction side 20, leading edge 22 and trailing edge 24.

During operation of the engine, vanes 12a, 12b, 12c and 12d may develop cracks, chips and other defects. Other portions of vane assembly 10 may also develop cracking and similar defects. As such, vane assembly 10 may be removed from the engine to repair the cracks and defects, and to perform other maintenance. A braze repair process, such as a TURBOFIX® repair, or similar methods of activated diffusion bonding, may be used to repair vanes 12a, 12b, 12c and 12d. The braze repair is a blend of several metals, including, but not limited to, nickel, chromium, cobalt, tungsten, aluminum and boron. A significant portion of the blend may be made up of the base metal in the alloy used to form vane assembly 10. In the exemplary embodiment of FIGS. 1A and 1B, the base metal is nickel. The braze repair may be applied as a powder, viscous paste, paint, transfer tape, controlled density tape, and plate produced from powder.

After application of the braze alloy to assembly 10, a heat treatment is used to bond the braze alloy to the surfaces of assembly 10 to which it is applied. The braze repair process is intended to restore assembly 10 into an acceptable condition for return to service in an engine. However, the TURBOFIX® process may result in lowering an incipient melting temperature of the metal alloy due to a diffusion of boron into the base metal alloy. More specifically, if vane assembly 10 has undergone more than one TURBOFIX® repair, boron levels increase in the nickel alloy, and, at some point, the boron saturates the base nickel alloy. As a result, an increased concentration of embrittling borides may form in the nickel alloy. Moreover, incipient melting may occur due to an influence of boron in lowering the incipient melting point of the base nickel alloy.

When the metal alloy is heated to a certain temperature, melting of the metal alloy begins to occur (i.e. incipient melting). Once the metal alloy cools, it then solidifies, resulting in voids in the microstructure, which weaken the structural integrity of the metal alloy. As described further below, the voids in the metal are visible as black or dark spots in a magnified image of the microstructure. Because the melting occurs as a result of boron saturation, the voids are often observed in areas where the metal alloy is concentrated with borides. It is recognized that the incipient melting point may vary across vane assembly 10 depending on where, and how many times, the braze alloy is applied.

In some cases, a braze alloy repair may be performed only once on a vane assembly. In other cases, a second or third braze alloy repair may be performed; however, the vane assembly, or other turbine component, typically requires additional testing or steps before an additional braze repair is approved.

Assuming vanes 12a, 12b, 12c and 12d already underwent at least one TURBOFIX® repair, it is necessary to determine if incipient melting has occurred on vanes 12a, 12b, 12c or 12d before performing a subsequent repair. Although incipient melting is focused on herein, it is recognized that vane assembly 10 may be inspected for other features before deciding to proceed with the repair process. For example, before inspecting vanes 12 for incipient melting, vane assembly 10 may undergo dimensional inspections to ensure that areas of vanes 12 were not damaged during operation. A magnified image of a microstructure of one of vanes 12 is necessary to determine the presence of incipient melting. However, this used to require that a portion of vane 12a, 12b, 12c or 12d be placed under a microscope to produce the magnified image. In most cases, this used to require that a micro (i.e. a metal sample) be taken from a surface of one of vanes 12 that had the braze alloy applied to it. A disadvantage of this technique is that the metal sample or micro is cut out of one of vanes 12. In order for vane assembly 10 to be returned to operation or service in an engine, the removed material needs to be reinserted or replaced. In either case, to insert the material into the vane, whether it is the original metal sample or a replacement piece of metal, it must be welded and heat treated. In some cases, it may be too difficult to restore the vane, and that particular vane or vane assembly may be scrapped. This destructive method of inspecting vane assembly 10 is time consuming and costly.

A non-destructive method of inspecting vane assembly 10 for incipient melting is described herein. A replicating material may be placed on a surface of vane assembly 10 to create an inverted replica of the microstructure. As shown below, this method yields the same results as compared to if a metal sample was removed from assembly 10 to create a micro.

In the embodiment shown in FIGS. 1A and 1B, vane assembly 10 includes four airfoils or vanes 12. It is recognized that the inspection method described herein may be used on a vane assembly or nozzle segment having more or less than four airfoils. Moreover, the inspection method may also be used for other gas turbine engine parts that may be repaired with the TURBOFIX® process or similar repair processes.

Figure 2:
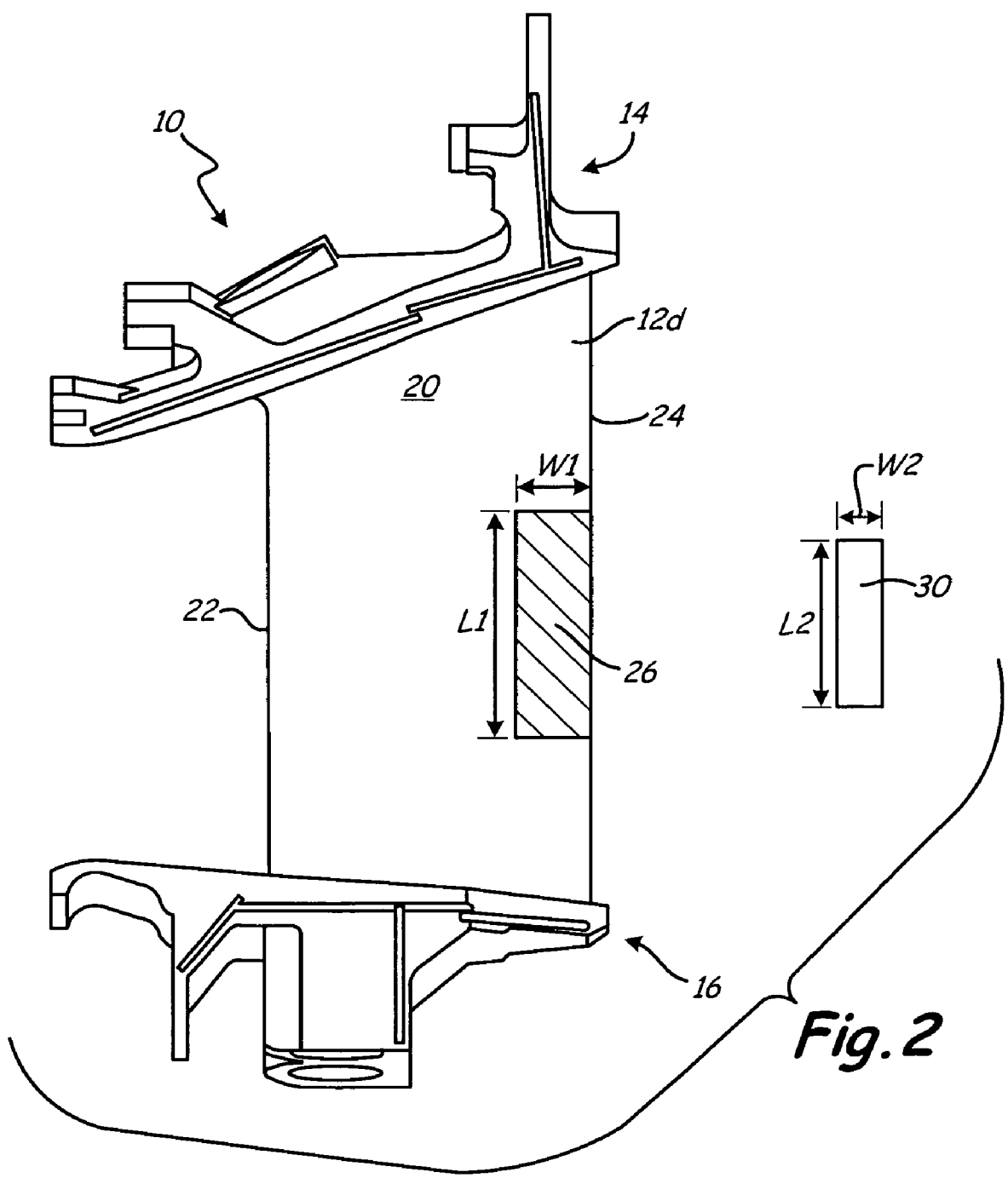
FIG. 2 is a side view of a vane from the vane assembly of FIGS. 1A and 1B.

FIG. 2 is a side view of vane assembly 10 and replicating material 30. Assembly 10 is rotated counter-clockwise approximately 90 degrees relative to FIG. 1B. As shown in FIG. 2, vane assembly includes shroud 14, platform 16, and suction side 20 of fourth vane 12d, having leading edge 22 and trailing edge 24. To determine whether incipient melting has occurred on vane 12d, as well as on other areas of vane assembly 10, a representative section of vane 12d is selected as a replication surface. The representative section is one that is commonly cracked or degraded and mostly likely already underwent the braze alloy repair. In an exemplary embodiment, trailing edge 24 on suction side 20 of outer vane 12d is selected. The metal alloy for this area of vane 12d may be thinner than other areas of vane assembly 10. This is significant because boron from the crack repair process may saturate a thinner section of the metal alloy more quickly. Thus, if incipient melting has occurred on vane assembly 10, it is probable that it occurs at least on trailing edge 24 of suction side 20. Surface 26 represents a replication inspection area for vane assembly 10.

In an exemplary embodiment, the replication inspection area (i.e. surface 26) has length L1 of approximately 1.25 inches (3.175 centimeters) and width W1 of approximately 0.25 inches (0.64 centimeters). Replicating material 30 is designed to be placed on surface 26. In an exemplary embodiment, replicating material has length L2 equal to at least 1.0 inch (2.54 centimeters) and width W2 equal to at least 0.2 inches (0.51 centimeters). It is recognized that material 30 may be larger than the embodiment shown in FIG. 2.

Prior to placing replicating material 30 on surface 26, surface 26 is prepared for replication. The preparation steps include etching, which may, in some cases, lead to crack propagation. As such, an area on vane 12d surrounding surface 26 may be masked using plastic film tape. The tape may also be used to protect airfoil cooling holes and other airfoil core openings. As an alternative to using tape, a fixture device may be designed such that only surface 26 of vane 12d is exposed for preparation. The fixture acts as a barrier for the non-replicating surfaces of vane 12d, which are thus protected from the preparation steps described herein. Replication surface 26 is then ground and polished to create a smooth surface. The specifics of the process depend on a roughness of surface 26. For example, in some cases, the process begins with 80 grit aluminum oxide paper; and in other instances, if surface 26 is fairly smooth, the process begins with 240 grit paper. Next, surface 26 is polished using, for example, diamond paste and a lubricant solution, such as Varsol. After polishing, surface 26 is then cleaned with acetone, followed by chemical etching. As commonly done in a microstructural evaluation, the etching process is performed on surface 26 to reveal the metal grain and phase structure on surface 26.

At this stage, replicating material 30 may be placed on surface 26 to create an inverted replica of the microstructure of surface 26. In one embodiment, replicating material 30 is cellulose acetate. More specifically, in the exemplary embodiment of FIG. 2, replicating material 30 is a cellulose acetate film.

Another suitable replicating material includes, but is not limited to, collodion, which is a nitrocellulose solution (also known as proxylin solution). Collodion is applied as a liquid to surface 26. The liquid dries on surface 26 to form a film that may then be peeled off of surface 26. In some cases, a replica created using collodion may not provide as detailed of an image of the microstructure, compared to a replica made with cellulose acetate. It is recognized that other materials capable of creating a replica of the microstructure of the metal may be used in the method described herein.

To attach replicating material 30 to surface 26, acetone is first applied to surface 26. In this second application of acetone to surface 26, a reagent grade acetone is used. A sufficient amount of time is permitted to allow the acetone to dry on surface 26.

Replicating material 30 may be applied to surface 26 using a pair of tweezers or an equivalent device. Immediately before applying material 30, acetone may be applied yet again to surface 26. Once replicating material 30 is placed on surface 26, material 30 is left on for a sufficient amount of time for material 30 to dry. The time may vary depending on a thickness of material 30. An appropriate time range may be between three and ten minutes.

Replicating material 30 may then be peeled off of surface 26. (The tweezers may also be used during this removal step.) Material 30 is then placed on a glass slide which may be placed under a microscope. Material 30 is oriented on the slide such that a side of material 30 that contacted surface 26 is oriented facing up on the slide. In some embodiments, scotch tape may be used near corners of replicating material 30 to hold material 30 down on the slide.

A magnified photograph of replicating material 30 is then taken in order to view the microstructure of surface 26 of vane 12*d* and evaluate whether incipient melting has occurred in the metal alloy. In some embodiments, material 30 may be chrome coated or sputtered in order to provide better resolution of the microstructure of surface 26; however, this step is not required. Based on an evaluation of the magnified image, which includes a comparison with acceptable microstructure samples, a decision may be made as to whether vane assembly 10 may undergo the repair process and then be returned to the engine.

A test study was done to compare a magnified image of a destructive metallographic sample to a non-destructive film replica of the same area. The test study was performed on a low pressure turbine (LPT) blade, formed from a cast nickel base superalloy, which had undergone the TURBOFIX® repair process four times. The LPT blade was subject to an additional heat treatment at 2250 degrees Fahrenheit (1232 degrees Celsius) for one hour in a vacuum in order to promote melting of the nickel base superalloy.

A micro was formed by cutting out a sample from a leading edge of the LPT blade. In order to create a replica, a surface of the micro was prepared as the replication surface. The surface was polished using progressively finer grit papers, starting with 80 aluminum oxide grit, proceeding to 240, 400, 600 and finishing with 2400 aluminum oxide grit. Two papers per grit were used for polishing. Following polishing, a 6 micro diamond paste was applied using a low nap or canvas polishing cloth.

The polished surface was then cleaned with acetone and swab etched with mixed reagent grade acids. The surface was rinsed with water, followed by application of reagent grade acetone. Cellulose acetate film was then applied to the surface, and allowed to dry for at least three minutes. Using metallic tweezers, the cellulose acetate film was removed and mounted on a glass slide with the contact surface facing up.

FIGS. 3A and 3B are photographs of the replica from the test study. FIGS. 4A and 4B are photographs of the actual metal sample (i.e. the micro) that was destructively removed from a leading edge of the LPT blade. FIGS. 3A and 4A are magnified 200 times; FIGS. 3B and 4B are magnified 500 times.

In both FIGS. 3A and 4A, a circle contains an area where incipient melting occurred. The circled area is further magnified in FIGS. 3B and 4B to better illustrate incipient melting in the nickel based superalloy. The dark spot in the images represents a void in the metal, which is caused by melting. Note that the replication process results in an inverted image compared to images taken from an actual metal sample. Bubbles that formed in the replicating film are visible in the replicated images of FIGS. 3A and 3B, particularly in FIG. 3A.

The magnified images in FIGS. 3A, 3B, 4A and 4B validate that the replication method described herein results in an accurate representation of the microstructure of the metal alloy. Incipient melting is discernible in both FIGS. 3A and 3B. Other features of the microstructure, such as eutectic phases, are also visible in FIGS. 3A and 3B.

A second test study was performed to evaluate a microstructure on an LPT vane assembly, similar to vane assembly 10 shown in FIGS. 1A-1B and 2. More specifically, the selected replication area on the LPT vane assembly in the second test study was in an area similar to the replication inspection zone of FIG. 2, designated as surface 26. Thus, the replica of the second test study was created by placing cellulose acetate film on a trailing edge on a suction side of an outer LPT vane. The surface of the vane was first prepared using the steps described above.

Figure 5A:
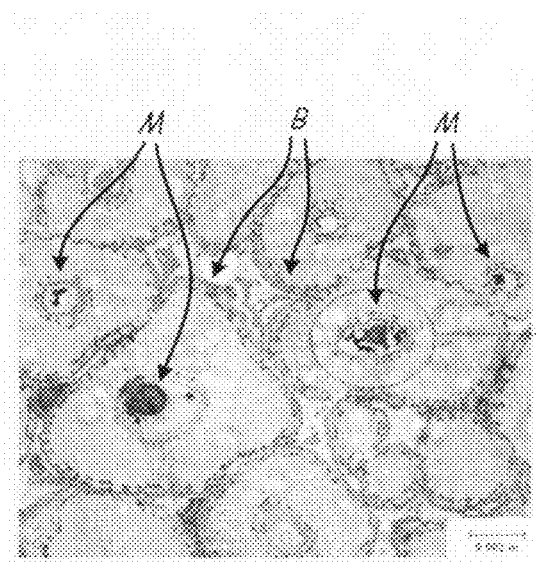
FIGS. 5A and 5B are magnified photographs of a replicated image of a microstructure of a second metal alloy part.
Figure 5B:
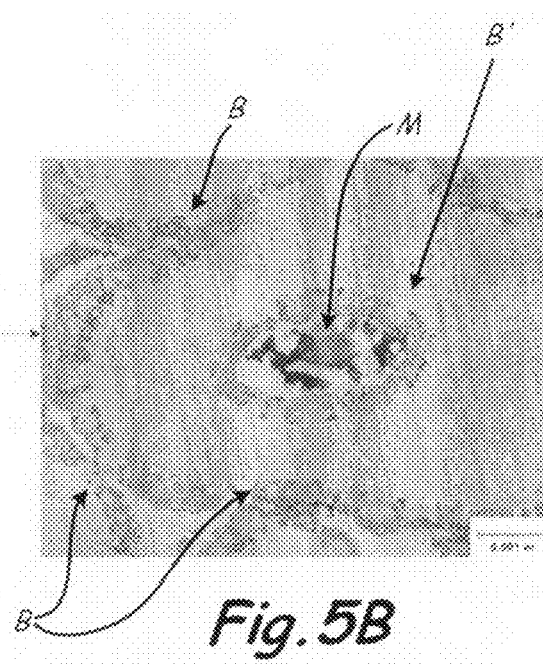

FIGS. 5A and 5B are photographs of the second replicated image, magnified 200 times and 500 times, respectively. Similar to above, the circled area in FIG. 5A is further magnified in FIG. 5B. The dark spots in FIGS. 5A and 5B, indicated by arrows M, are voids in the metal alloy, which form after the metal alloy had begun to melt. The irregular circles in FIGS. 5A and 5B, which look similar to cells and some of which are labeled with arrows B, indicate areas of boride concentration. As described above, boron is commonly contained in the braze alloy blend and contributes to decreasing the incipient melting temperature of the base metal alloy with each iteration of the TURBOFIX® process. As shown in FIG. 5A, the voids are contained within the irregular circles. Moreover, as shown in FIG. 5B, the void is surrounded by a smaller irregular circle, labeled B', which also represents the formation of borides on the surface of the metal alloy in an area that immediately surrounds the void. Smaller irregular circles immediately surrounding the other voids are also visible in FIG. 5A.

FIGS. 5A and 5B further illustrate that a replicated image of the surface of a metal alloy part is sufficiently clear to evaluate a microstructure of the metal alloy. Moreover, FIGS. 5A and 5B show that incipient melting and areas of boron concentration are discernible from a replicated image. Therefore, a non-destructive replicating material, such as cellulose acetate, may be used as an alternative to a destructive micro.

Once the replicated image of the microstructure of a metal alloy is obtained, the replicated image may be evaluated to determine whether the metal alloy part may undergo the crack repair process before being returned to service. If it is determined that incipient melting has already occurred, due to a previous repair, then the metal alloy part is not in an acceptable condition to be returned to service. In that case, the part may be deemed non-repairable. In contrast, if incipient melting is not observed in the replicated image, then the TURBOFIX® process may be performed on the part, even if the part has previously been repaired one or more times. For an airfoil, like vane 12d of FIG. 2, the replicating material is placed on the airfoil in an area that commonly experiences cracking, and then consequently is repaired. If incipient melting is not observed in the base metal alloy in that area of the airfoil, then it follows that incipient melting has likely not occurred on the vane assembly or nozzle segment.

Evaluation of the metal alloy part may include comparing the magnified image on the replicating material to other images of metal alloy samples. Samples that are deemed as unacceptable, and thus non-repairable, are metal samples having any level of incipient melting. As described above, incipient melting is visible as black or dark spots on the magnified image. The black spots are usually located in proximity to areas of boride concentration, which may be identified as irregular cell-like shapes. Moreover, as shown in FIG. 5B, the black spot (i.e. a void) is commonly enclosed in a smaller irregular circle, labeled B', which is borides forming on a surface of the base nickel alloy. Incipient melting of the base metal alloy is observable to metallurgists and others skilled in the art. The sample in FIGS. 5A and 5B is an example of a sample that is defined as unacceptable due to incipient melting.

Samples that are defined as being acceptable, and in condition for repair, include samples without voids or pores in the microstructure. As described above, the boron saturates the base metal alloy as additional amounts of boron are added to the metal surface, as a result of the braze alloy material. Thus, the formation of borides in the base metal alloy progresses, either as more material is applied in one TURBOFIX® repair, or as additional TURBOFIX® repairs are performed. Acceptable samples may, in some cases, include those having varying amounts of boride concentration, so long as voids are not present. In some embodiments, a sample having a high concentration of borides may be classified as an unacceptable sample. As stated above, evaluation of a replicated image may be made by one skilled in the art and using known examples of acceptable and unacceptable samples.

As described herein, any level of incipient melting is not acceptable, and an engine part is deemed non-repairable if incipient melting is observed. However, it is recognized that, in alternative embodiments, some level of incipient melting may be acceptable, depending, for example, on the type of part being inspected.

The replication method described herein allows a replicated image of a metal alloy surface to be easily created without causing any destruction to a metal part. In the case in which the replicated image is unsatisfactory, another replica can easily be created. This method allows essentially every repaired engine part to be inspected when it is brought to a service or repair area, regardless of how many times the part has previously been repaired. Moreover, it is no longer necessary for a representative part to be sacrificed to determine serviceability of a group of parts.

This method of using a replicating material to create a replica of a metal surface is described in the context of a vane assembly of a low pressure turbine or a high pressure turbine of an aircraft engine. It is recognized that this method may be used for other metal parts, such as other parts within an aircraft engine, including other types of non-aero metal parts that may undergo the TURBOFIX® process or similar crack repair processes. The inspection method is described herein in the context of determining whether incipient melting has occurred in a metal alloy. It is recognized that the inspection method may also be used for evaluating other features in the microstructure of the metal alloy.

Although the present invention has been described with reference to preferred embodiments, workers skilled in the art will recognize that changes may be made in form and detail without departing from the spirit and scope of the invention.

The invention claimed is:

1. A method of inspecting a repaired metal part to determine whether further repair is appropriate, the method comprising:
    placing a replicating material on a surface of the metal part to create an inverted replica of a microstructure of the surface;
    removing the replicating material from the surface of the metal part;
    magnifying an image of the inverted replica on the replicating material; and
    analyzing the image to determine whether an area of boron concentration is present on the metal part.

2. The method of claim 1 further comprising:
    determining whether the metal part can be repaired and returned to service based on an amount of boron concentration present on the metal part.

3. The method of claim 1 further comprising:
    inspecting the image for a presence of voids in a base metal alloy of the metal part.

4. The method of claim 1 wherein the replicating material is cellulose acetate.

5. The method of claim 1 wherein the replicating material is collodion.

6. The method of claim 1 further comprising:
    applying a chrome coating to the replicating material after removing the replicating material from the surface.

7. The method of claim 1 further comprising:
    preparing the surface of the metal part prior to placing the replicating material on the surface.

8. The method of claim 7 wherein preparing the surface of the metal part includes polishing the surface using at least one grit paper.

9. The method of claim 7 wherein preparing the surface of the metal part includes applying acetone to the surface.

10. The method of claim 7 wherein preparing the surface of the metal part includes chemically etching the surface.

11. The method of claim 1 wherein the metal part is a component of a gas turbine engine.

12. The method of claim 11 wherein the metal part is a turbine vane assembly of a gas turbine engine.

13. The method of claim 11 further comprising:
    comparing the image to samples of metal alloys to determine if the metal part may be returned to service in a gas turbine engine, wherein the samples include at least one unacceptable sample having incipient melting and at least one acceptable sample without incipient melting.

14. A method of analyzing a microstructure of a metal alloy part used in a gas turbine engine, the method comprising:
    preparing a surface of the metal alloy part;
    placing a replicating material on the surface of the metal alloy part;
    leaving the replicating material on the surface of the metal alloy part for a time sufficient to create an inverted replica of the microstructure of the metal alloy part;
    removing the replicating material from the surface of the metal alloy part; and evaluating a magnified image of the inverted replica to determine whether an area of boron concentration is present on the metal alloy part.

15. The method of claim 14 wherein the replicating material includes at least one of cellulose acetate and collodion.

16. The method of claim 14 wherein preparing the surface of the metal alloy part includes at least one of grinding, polishing, etching, and applying acetone.

17. The method of claim 14 wherein evaluating the magnified image of the inverted replica includes determining a presence of voids in the microstructure and determining a presence of borides in the microstructure.

18. The method of claim 14 further comprising:
comparing the magnified image to a set of metal alloy samples including acceptable samples without incipient melting and unacceptable samples having incipient melting; and
determining whether the metal alloy part may be returned for use in a gas turbine engine.

19. The method of claim 14 wherein the metal alloy part is a turbine vane.

20. A method of evaluating a metal alloy of a gas turbine engine airfoil to determine if incipient melting has occurred as a result of a braze alloy repair, the method comprising:
preparing a surface of the airfoil;
applying a replicating material to the surface of the airfoil for a time sufficient to create an inverted replica of a microstructure of the airfoil on the replicating material; and
magnifying an image of the inverted replica to determine if incipient melting has occurred in the metal alloy of the airfoil as a result of the braze alloy repair by inspecting the inverted replica for an area of boron concentration.

21. The method of claim 20 wherein preparing the surface of the airfoil includes at least one of grinding, polishing, chemical etching, and applying acetone to the surface.

22. The method of claim 20 wherein the time sufficient to create an inverted replica of the microstructure of the airfoil is between approximately three and ten minutes.

23. The method of claim 20 wherein the metal alloy is a nickel alloy.

24. The method of claim 20 wherein the replicating material includes at least one of cellulose acetate and collodion.

25. The method of claim 20 wherein determining if incipient melting has occurred further comprises evaluating a presence of voids in the metal alloy.

26. The method of claim 20 further comprising:
comparing the magnified image of the inverted replica to a set of metal alloy samples to evaluate whether the metal airfoil is in an acceptable condition to be returned to service in a gas turbine engine, wherein the set of metal alloy samples includes at least one acceptable sample having no incipient melting and at least one unacceptable sample having incipient melting.

* * * * *